(12) United States Patent
Mashio et al.

(10) Patent No.: US 8,777,617 B2
(45) Date of Patent: Jul. 15, 2014

(54) DENTAL ABUTMENT

(75) Inventors: Go Mashio, Itabashi-ku (JP); Fumiya Sato, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/482,467

(22) Filed: May 29, 2012

(65) Prior Publication Data

US 2012/0308960 A1 Dec. 6, 2012

(30) Foreign Application Priority Data

May 31, 2011 (JP) ................................. 2011-121723

(51) Int. Cl.
*A61C 8/00* (2006.01)
(52) U.S. Cl.
USPC .......................................... 433/173
(58) Field of Classification Search
USPC .................................... 433/173, 174
See application file for complete search history.

(56) References Cited

U.S. PATENT DOCUMENTS

| 5,104,318 | A * | 4/1992 | Piche et al. | 433/174 |
| 6,244,867 | B1 * | 6/2001 | Aravena et al. | 433/172 |
| 6,672,871 | B2 * | 1/2004 | Hurson | 433/172 |
| 6,910,891 | B2 * | 6/2005 | Carroll | 433/173 |
| 8,235,722 | B2 * | 8/2012 | Pfeiffer et al. | 433/183 |
| 2006/0257823 | A1 * | 11/2006 | Pfeiffer et al. | 433/218 |
| 2009/0298014 | A1 | 12/2009 | Jandali et al. | |
| 2010/0266985 | A1 | 10/2010 | Yau et al. | |
| 2010/0311011 | A1 | 12/2010 | Schwieder et al. | |

FOREIGN PATENT DOCUMENTS

| EP | 1 269 932 | 1/2003 |
| JP | 2007-222225 | 9/2007 |
| WO | WO 2004/073541 | 9/2004 |

OTHER PUBLICATIONS

Extended European Search Report dated Aug. 28, 2012 in corresponding European patent application No. 12004168.6.

* cited by examiner

*Primary Examiner* — Ralph Lewis
(74) *Attorney, Agent, or Firm* — Oblon, Spivak, McClelland, Maier & Neustadt, L.L.P.

(57) ABSTRACT

To provide a dental abutment having an embedded part embedded into an embedding hole of a block and fixed in the embedding hole. An uniform gap for a dental adhesive can be formed along an approximately entire circumference between an outer peripheral surface of the embedded part and an inner surface of the embedding hole. The dental abutment includes a gingiva contact part 1 having a forward-thicker truncated conical shape on the intraoral side; a fitting part 2 projecting toward the jawbone side from the jawbone-side contact surface 1a of the gingiva contact part 1, and fitted into an end part on the intraoral side of the implant fixture so as not to rotate; and an embedded part 3 to be embedded. Three or more projecting line parts 5 are formed on an outer peripheral surface 3a of the embedded part 3 so as to form the uniform gap.

8 Claims, 3 Drawing Sheets

DENTAL ABUTMENT

BACKGROUND OF THE INVENTION

1. Field of the Invention

The present invention relates to a dental abutment, which is fitted to the intraoral side of an implant fixture embedded in a jawbone and is fixed at the implant fixture with a bolt penetrating a through hole provided to be coaxial with a center axis. The dental abutment can strongly bond and fix a dental prosthesis, which is produced from cutting a ceramics block, to an accurate position based on three-dimensional shape data, (where the dental prosthesis includes members for a dental prosthesis, such as coping and the like).

2. Description of the Conventional Art

As a method of producing a lot of dental prostheses having stable quality for a short time as much as possible while reducing the burden to a dental technician, a dental CAD/CAM system has been developed in recent years. The dental CAD/CAM system is to produce a dental prosthesis by using a three-dimensional measuring apparatus, a computer or the like to create three-dimensional shape data of a dental prosthesis such as an inlay, a crown, a bridge, a coping, or the like, and cutting a block by an automatic cutting machine based on the three-dimensional shape data of the dental prosthesis.

When a dental prosthesis to be attached to the intraoral side of an implant fixture is produced by the dental CAD/CAM system, a different technique from an inlay or a crown is necessary. That is, the dental prosthesis for a dental implant is different from a dental prosthesis such as an inlay, a crown, or the like, and in the production of the dental prosthesis for a dental implant, it is necessary to produce a dental prosthesis capable of being strongly fixed at an accurate position of a dental abutment, so that the dental prosthesis can be placed and fixed at a position as planned, where the dental abutment is fitted to the intraoral side of an implant fixture embedded in a jawbone and fixed at the implant fixture with a bolt penetrating a through hole provided to be coaxial with a center axis.

A metallic dental prosthesis has been conventionally used as the dental prosthesis for a dental implant produced by the dental CAD/CAM system. Thus, since there is no problem in strength, the dental prosthesis is just produced to externally fitted to an accurate position of a dental abutment, which is fitted to the intraoral side of an implant fixture embedded in a jawbone and fixed at the implant fixture with a bolt penetrating a through hole provided to be coaxial with a center axis. However, in recent years, the dental prosthesis for a dental implant produced by the dental CAD/CAM system is made of ceramics such as zirconia or the like in recent years, so that the beauty appearance is not spoiled at a time of deterioration of gingiva after a dental implant treatment.

However, if ceramics such as zirconia or the like is used for a material of the block, the ceramics block is a sintered compact, and the degree of shrinkage generating after sintering is different in places, so that there is a problem that it is difficult to form the dental prosthesis to be externally fitted to the accurate position of the dental abutment after sintering. In addition, there is also a problem that the strength at a portion to be externally fitted to the dental abutment may be lacked in the ceramics dental prosthesis.

Present inventors have invested a method of producing a dental prosthesis to solve problems in the production of a dental prosthesis for a dental implant with the dental CAD/CAM system (refer to Japanese Patent Application Laid-Open No. 2007-222225). The method solves a problem that it is difficult to maintain a shape of a fitting part with desired dimensional accuracy after sintering of ceramics such as zirconia or the like, and a problem that the strength of the fitting part may be lacked in ceramics such as zirconia or the like. In the method, a separate part having a fitting part formed to be fitted to an implant fixture is produced in advance, and an embedding part of the separate part is embedded into an embedding hole and fixed, where the embedding hole is formed in advance at a block for a dental prosthesis or formed when cutting the block to be a dental prosthesis. Then, the fitting part to be fitted to the implant fixture is used in a state of projecting.

When the separate part is used, it is necessary to strongly fix the separate part to the block. For example, it is necessary to cut the separate part of a dental abutment or the like and an embedding hole formed at the block in advance or the like with high accuracy, insert an embedding part of the separate part of a dental abutment or the like into the embedding hole of the block, and strongly bond and fix the separate part with an dental adhesive or the like. The reason of this is as follows. That is, in case of the block made of ceramics such as zirconia, which has been widely used in recent years, the strength of the fitting part may be lacked. So, only by fitting a concave part provided at the embedding hole of the block to a projection part provided at the embedded part of the separate part of a dental abutment or the like, the block cannot be prevented from breaking in many cases.

In such a case of adhering and fixing, it is important that a gap for a dental adhesive is kept certainly between the embedding hole formed in the block and the embedded part of a dental abutment or the like, and that the embedded part of a dental abutment or the like is positioned and fixed in the embedding hole of the block. That is, since sufficient adhesive strength cannot be obtained if the coated dental adhesive is too thick, it is necessary to certainly form the gap so that the dental adhesive comes to be an uniformly desired thin layer. However, for example, only by cutting a cylindrical embedding hole and a columnar embedded part, coating an adhesive to an inner surface of the embedding hole and an outer peripheral surface of the embedded part, and inserting the embedded part into the embedding hole, the embedded part with a small diameter is freely moved in the embedding hole with a large diameter. Thus, it is very difficult to form a layer of the adhesive with an uniform thin thickness over an approximately entire circumference between the inner surface of the embedding hole and the outer peripheral surface of the embedded part. Therefore, it is necessary to enable to position and fix the embedded part of a dental abutment or the like in the embedding hole of the block.

SUMMARY OF THE INVENTION

The present invention is to solve the aforementioned problems, and an objective of the present invention is to provide a dental abutment having an embedded part which is embedded into an embedding hole of a block (a dental prosthesis) and bonded and fixed. In the dental abutment, the embedded part is positioned and fixed in the embedding hole of the block. In addition, an uniform gap for a dental adhesive can be formed along an approximately entire circumference between an outer peripheral surface of the embedded part and an inner surface of the embedding hole of the block.

The present inventors carried out earnest works to solve the aforementioned problems and, as a result, they found the following to complete the present invention. That is, a dental abutment is formed to include a gingiva contact part, which is formed to have a forward-thicker truncated conical shape on the intraoral side from a jawbone-side contact surface being in contact with an intraoral-side end surface of an implant fixture. The dental abutment also includes a fitting part, which is provided projecting toward the jawbone side from the jawbone-side contact surface of the gingiva contact part, and fitted into an end part on the intraoral side of the implant fixture so as not to rotate. The dental abutment yet also includes an embedded part, which is provided projecting toward the side opposite to the fitting part from the intraoral-side surface of the gingiva contact part, and is embedded into an embedding hole, which is formed in advance at a ceramics block for a dental prosthesis or formed when cutting the ceramics block to be a dental prosthesis. Accordingly, when the embedded part is embedded into the embedding hole of the block (a dental prosthesis), the intraoral-side surface of the forward-thicker gingiva contact part functions as a stopper, so that the embedded part is not embedded into the embedding hole too much but can be embedded to a correct depth.

Further, a through hole in which a bolt screwed into a female thread screwed in the implant fixture is inserted to penetrate is formed so as to penetrate the fitting part, the gingiva contact part, and the embedded part. In addition, a step part being in contact with a head of the bolt is formed in the through hole, and a center axis of the through hole is provided to be coaxial with center axis of the gingiva contact part, the fitting part and the embedded part. Accordingly, a dental prosthesis integrated with the dental abutment can be attached strongly and accurately to the implant fixture by the bolt inserted into the through hole. In addition, the head of the bolt is not in contact with the block which has a problem in its strength because of being made of ceramics.

Further, three or more projecting line parts having a same shape are formed on an outer peripheral surface of the embedded part. Each of the projecting line parts starts from the end part on the side of the gingiva contact part, and its longitudinal direction is in parallel with the center axis of the embedded part. Each top part of the projecting line parts is in contact with a bottom part of a concave groove formed in the embedding hole when block being embedded into the embedding hole of the ceramics block, so that the uniform gap for a dental adhesive can be formed along the approximately entire circumference between the inner surface of the embedding hole and the outer peripheral surface of the embedded part. In one or two of the projecting line parts, even if the embedded part of the dental abutment is inserted into the embedding hole of the block (the dental prosthesis), there are few contact points, so that the embedded part is freely moved in the embedding hole, and the gap for a dental adhesive having an uniform width cannot be formed. However, since three or more projecting line parts are provided on the outer peripheral surface of the embedded part, the embedded part of the dental abutment can be positioned and fixed in the embedding hole of the block (the dental prosthesis), and the gap for a dental adhesive having an uniform width can be certainly formed between the outer peripheral surface of the embedded part not having the projecting line part and the inner surface of the embedding hole of the block (the dental prosthesis) opposite to the outer peripheral surface of the embedded part not having the projecting line part. In addition, the top parts of the three of more projecting line parts of the dental abutment are respectively in contact with the bottom part of the concave groove formed in the embedding hole, so that each of the projecting line parts is induced along the concave groove to be positioned and fixed. Thus, the dental abutment can be certainly inserted into a predetermined position.

Further, they also found out the following. That is, if the width of the gap for a dental adhesive is set to be 5 to 100 μm, the dental adhesive can be formed sufficient-thinly, so that high bonding strength can be obtained. The projecting line part is formed to have a length of 0.05 to 3 mm, a width of 0.05 to 0.2 mm, and the maximum height from the outer peripheral surface of the embedded part of 0.01 to 0.2 mm. With such a configuration, when the embedded part of the dental abutment is inserted into the embedding hole of the block (the dental prosthesis), the uniform gap for a dental adhesive can be certainly formed along the approximately entire circumference between the inner surface of the embedding hole and the outer peripheral surface of the embedded part, so that sufficient bonding strength can be obtained. So, it is preferable.

Furthermore, the dental abutment is comparatively small. Thus, if the number of the projecting line parts formed on the outer peripheral surface of the embedded part is three at the minimum, the dental abutment can be machined comparative-easily, so that it is preferable. Further, in such an embodiment, if the projecting line parts are respectively formed at equal intervals so that an angle between adjacent projecting line parts can be 120°, the dental adhesive can be coated uniformly between the adjacent projecting line parts, so that the dental abutment can be certainly fixed at the block. So, it is preferable. Furthermore, if the projecting line parts are respectively formed so that the angles between the adjacent projecting parts are 150°, 150° and 60°, the position at which each of the projecting line parts is in contact with the concave groove of the embedding hole is only one. Thus, the attachment position of the dental abutment is not mistaken. In addition, having such angles, there are no parts where the intervals between the adjacent projecting line parts are not too narrow. Thus, the bonding strength is not reduced, so that it is preferable.

14The dental abutment according to the present invention is formed to include a gingiva contact part, which is formed to have a forward-thicker truncated conical shape on the intraoral side from a jawbone-side contact surface being in contact with an intraoral-side end surface of an implant fixture. The dental abutment also includes a fitting part, which is provided projecting toward the jawbone side from the jawbone-side contact surface of the gingiva contact part, and fitted into an end part on the intraoral side of the implant fixture so as not to rotate. The dental abutment yet also includes an embedded part, which is provided projecting toward the side opposite to the fitting part from the intraoral-side surface of the gingiva contact part, and is embedded into an embedding hole, which is formed in advance at a ceramics block for a dental prosthesis or formed when cutting the ceramics block to be a dental prosthesis. Accordingly, when the embedded part is embedded into the embedding hole of the block (a dental prosthesis), the intraoral-side surface of the forward-thicker gingiva contact part functions as a stopper, so that the embedded part is not embedded into the embedding hole too much but can be embedded to a correct depth.

Further, a through hole in which a bolt screwed into a female thread screwed in the implant fixture is inserted to penetrate is formed so as to penetrate the fitting part, the gingiva contact part and the embedded part. In addition, a step part being in contact with a head of the bolt is formed in the through hole, and a center axis of the through hole is provided to be coaxial with center axis of the gingiva contact part, the fitting part and the embedded part. With such a configuration, a dental prosthesis integrated with the dental abutment with the bolt inserted into the through hole can be attached strongly and accurately to the implant fixture. In addition, the head of the bolt is not in contact with the block which has a problem in its strength because of being made of ceramics.

Further, three or more projecting line parts having a same shape are formed on an outer peripheral surface of the embedded part. Each of the projecting line parts starts from the end part on the side of the gingiva contact part, and its longitudinal direction is in parallel with the center axis of the embedded part. Each top part of the projecting line parts is in contact with a bottom part of a concave groove formed in the embedding hole when block being embedded into the embedding hole of the ceramics block, so that the uniform gap for a dental adhesive can be formed along the approximately entire circumference between the inner surface of the embedding hole and the outer peripheral surface of the embedded part. In one or two of the projecting line parts, even if the embedded part of the dental abutment is inserted into the embedding hole of the block (the dental prosthesis), there are few contact points, so that the embedded part is freely moved in the embedding hole, and the gap for a dental adhesive having an uniform width cannot be formed. However, since three or more projecting line parts are provided on the outer peripheral surface of the embedded part, the embedded part of the dental abutment can be positioned and fixed in the embedding hole of the block (the dental prosthesis), and the gap for a dental adhesive having a uniform width can be certainly formed between the outer peripheral surface of the embedded part not having the projecting line part and the inner surface of the embedding hole of the block (the dental prosthesis) opposite to the outer peripheral surface of the embedded part not having the projecting line part. In addition, the top parts of the three of more projecting line parts of the dental abutment are respectively in contact with the bottom part of the concave groove formed in the embedding hole, so that each of the projecting line parts is induced along the concave groove to be positioned and fixed. Thus, the dental abutment can be certainly inserted into a predetermined position.

Further, in an embodiment that the width of the gap for a dental adhesive is set to be 5 to 100 μm, the dental adhesive can be formed sufficient-thinly, so that high bonding strength can be obtained. The projecting line part is formed to have a length of 0.05 to 3 mm, a width of 0.05 to 0.2 mm and the maximum height from the outer peripheral surface of the embedded part of 0.01 to 0.2 mm. With such a configuration, when the embedded part of the dental abutment is inserted into the embedding hole of the block (the dental prosthesis), the uniform gap for a dental adhesive can be certainly formed along the approximately entire circumference between the inner surface of the embedding hole and the outer peripheral surface of the embedded part, so that sufficient bonding strength can be obtained. So, it is preferable.

Furthermore, the dental abutment is comparatively small. Thus, if the number of the projecting line parts formed on the outer peripheral surface of the embedded part is three at the minimum, the dental abutment can be machined comparative-easily, so that it is preferable. Further, in such an embodiment, if the projecting line parts are respectively formed at equal intervals so that an angle between adjacent projecting line parts can be 120°, the dental adhesive can be coated uniformly between the adjacent projecting line parts, so that the dental abutment can be certainly fixed at the block. So, it is preferable. Furthermore, if the projecting line parts are respectively formed so that the angles between the adjacent projecting parts are 150°, 150° and 60°, the position at which each of the projecting line parts is in contact with the concave groove of the embedding hole is only one. Thus, the attachment position of the dental abutment is not mistaken. In addition, having such angles, there are no parts where the intervals between the adjacent projecting line parts are not too narrow. Thus, the bonding strength is not reduced, so that it is preferable.

Figure 1:
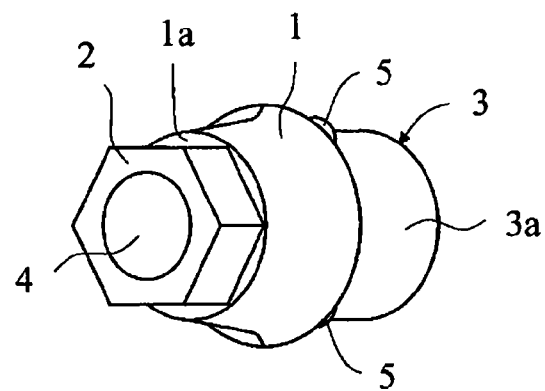
FIG. 1 is a perspective view illustrating one example of a dental abutment according to the present invention.
Figure 2:
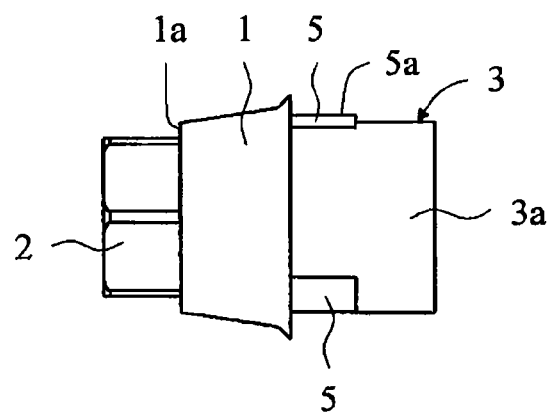
FIG. 2 is a front view of the dental abutment according to FIG. 1.

A dental abutment according to the present invention will be described in detail below with reference to the drawings.

A gingiva contact part 1 is formed to have a forward-thicker truncated conical shape on the intraoral side from a jawbone-side contact surface 1a being in contact with an intraoral-side end surface of an implant fixture. When an embedded part 3 described below is embedded into an embedding hole Ba of a dental prosthesis made of a block B, the intraoral-side surface of the forward-thicker gingiva contact part 1 functions as a stopper, so that the embedded part 3 is not embedded into the embedding hole Ba too much but can be embedded to a correct depth.

A fitting part 2 is provided projecting toward the jawbone side from the jawbone-side contact surface 1a, and fitted at an end part on the intraoral side of the implant fixture so as not to rotate. A embedded part 3 is provided projecting toward the side opposite to the fitting part 2 from the intraoral-side surface of the gingiva contact part 1, and is embedded into an embedding hole Ba, which is formed in advance at the ceramics block B for a dental prosthesis or formed when cutting the ceramics block B to be a dental prosthesis. The gingiva contact part 1, the fitting part 2, and the embedded part 3 are formed so that each center axis is coaxial.

In a through hole 4, a bolt screwed into a female thread screwed in the implant fixture is inserted to penetrate, and the through hole 4 is formed so as to penetrate the fitting part 2, the gingiva contact part 1 and the embedded part 3. In addition, a step part 4a being in contact with a head of the bolt is formed in the through hole 4, and a center axis of the through hole 4 is provided to be coaxial with center axis of the gingiva contact part 1, the fitting part 2, and the embedded part 3, so that the bolt inserted into the through hole 4 is positioned so as not to be uneven. Therefore, the dental prosthesis integrated with the dental abutment with the bolt inserted into the through hole can be attached strongly and accurately to the implant fixture. In addition, the head of the bolt is not in contact with the block which has a problem in its strength because of being made of ceramics.

Projecting line parts 5 having a same shape are formed on an outer peripheral surface of the embedded part 3. Each of the projecting line parts 5 starts from the end part on the side of the gingiva contact part 1, and its longitudinal direction is in parallel with the center axis of the embedded part 3. Each top part 5a of the projecting line parts 5 is in contact with a bottom part Bb of a concave groove formed in the embedding hole Ba when being embedded into the embedding hole Ba of the ceramics block B block, so that an uniform gap for a dental adhesive A can be formed along the approximately entire circumference between an inner surface Bc of the embedding hole Ba and an outer peripheral surface 3a of the embedded part 3.

The dental abutment according to the present invention has the three or more projecting line parts 5 on the outer peripheral surface 3a of the embedded part 3. In one or two projecting line parts, the embedded part 3 is freely moved in the embedding hole Ba, so that the gap for the dental adhesive A having an uniform width cannot be formed. However, since the three or more projecting line parts 5 are provided on the outer peripheral surface 3a of the embedded part 3, the embedded part 3 of the dental abutment can be positioned and fixed in the embedding hole Ba, and the gap for the dental adhesive A having an uniform width can be certainly formed between the outer peripheral surface 3a of the embedded part 3 not having the projecting line part 5 and the inner surface Bc of the embedding hole Ba of the block B opposite to the outer peripheral surface 3a of the embedded part 3 not having the projecting line part 5. In addition, the top parts 5a of the three of more projecting line parts 5 of the dental abutment are respectively in contact with the bottom part Bb of the concave groove formed in the embedding hole Ba, so that each of the projecting line parts 5 is induced along the concave groove. Thus, the dental abutment can be certainly inserted into a predetermined position.

Figure 3:
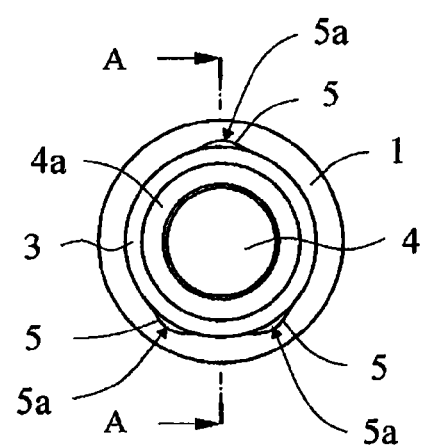
FIG. 3 is a right side view of the dental abutment according to FIG. 1.
Figure 4:
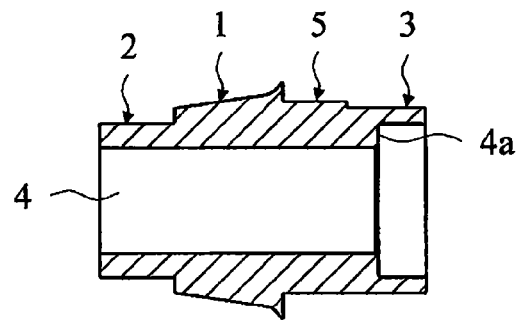
FIG. 4 is a cross-sectional view taken along the A-A line of the dental abutment according to FIG. 1.
Figure 6:
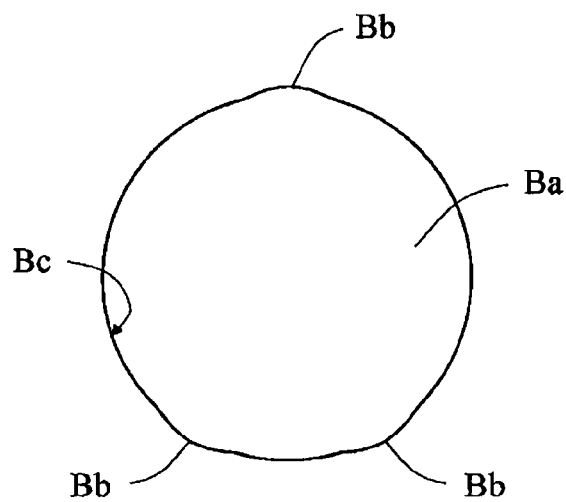
FIG. 6 is an enlarged view to explain the embedding hole of the block in FIG. 5.
Figure 7:
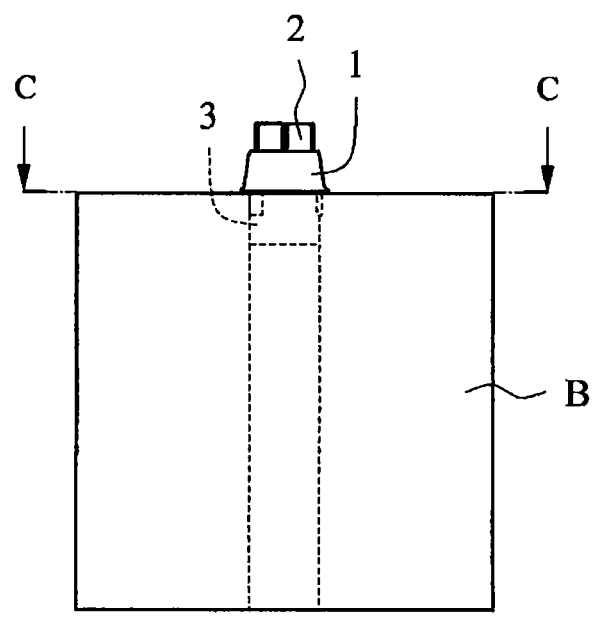
FIG. 7 is a front view to explain a state that an embedded part of a dental abutment according to FIG. 1 is embedded into an embedding hole of a block and bonded and fixed, where the block has a through hole for inserting an bolt, which is cut in advance.
Figure 8:
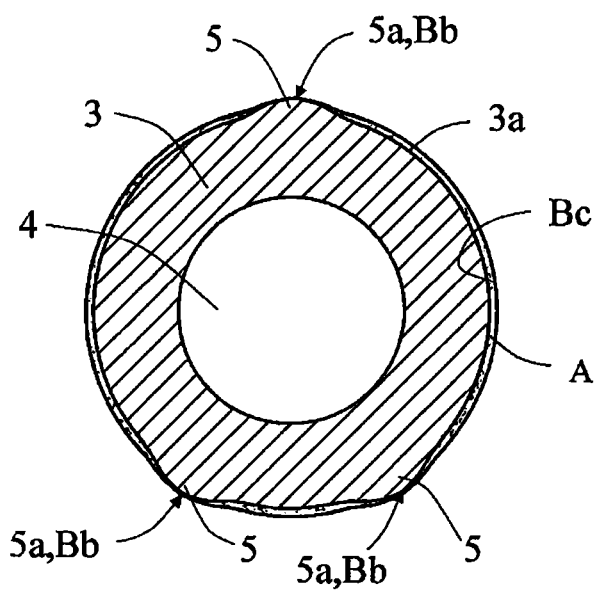
FIG. 8 is a cross sectional view to explain the positional relationship between the embedding hole of the block and the embedded part of the dental abutment in the C-C line in FIG. 7.

For example, the shape of such the projecting line part 5 can be a shape curving upward as illustrated in FIG. 3. Further, as illustrated in FIG. 6, if concave grooves each having the same shape as the projecting line part 5 is formed on the inner surface Bc of the embedding hole Ba of the block B, as illustrated in FIG. 8, the gap for the dental adhesive A having an uniform width can be certainly formed between the outer peripheral surface 3a of the embedded part 3 not having the projecting line part 5 and the inner surface Bc of the embedding hole Ba of the block B opposite to the outer peripheral surface 3a of the embedded part 3 not having the projecting line part 5, when the top part 5a of the projecting line part 5 is in contact with the bottom part Bb of the concave groove formed in the embedding hole Ba of the block B. Thus, the coated dental adhesive A can be uniformly applied along the approximately entire circumference.

If the width of the gap for the dental adhesive A is 5 to 100 μm, the dental adhesive A can be formed sufficient-thinly, and high bonding strength can be obtained, so that it is preferable. In addition, the reason why the width of the gap for the dental adhesive A is as follows. When the width of the gap for the dental adhesive A exceeds 100 μm, the dental adhesive A comes to be a thick layer, so that sufficient bonding strength cannot be obtained. When the width is less than 5 μm, the gap is too narrow. Thus, if processing accuracy is low, the gap cannot be formed depending on a place, and a portion on which the dental adhesive A is not coated occurs, so that the boding strength may be reduced extremely.

Further, the projecting line part 5 has the length of 0.05 to 3 mm, the width of 0.05 to 0.2 mm and the maximum height from the outer peripheral surface 3a of the embedded part 3 of 0.01 to 0.2 mm. With this configuration, when the embedded part 3 of the dental abutment is inserted into the embedding hole Ba, the gap for the dental adhesive A having the uniform width can be certainly formed along the approximately entire circumference between the inner surface Bc of the embedding hole Ba and the outer peripheral surface 3a of the embedded part 3, so that sufficient bonding strength can be obtained. So, it is preferable.

In addition, if the length of the projecting line part 5 is less than 0.05 mm, the length is too short. So, the embedded part 3 of the dental abutment may become a state of being in contact with the inner surface Bc of the embedding hole Ba at points, and the points function as a fulcrum, so that the embedded part 3 may be moved in the embedding hole Ba, centering on the fulcrum. If the length exceeds 3 mm, cutting need to be carried out with higher accuracy than necessary to form the gap for the dental adhesive A having the uniform width between the outer peripheral surface 3a of the embedded part 3 and the inner surface Bc of the embedding hole Ba when inserting such the long projecting line part 5. Further, if the width is less than 0.05 mm, the projecting line part 5 comes to be a thin plate state, so that the strength is lowered, and the dental abutment is easily broken. When the width exceeds 0.2 mm, the area ratio of the projecting line parts 5 to the outer peripheral surface 3a of the embedded part 3 increases too much, so that the dental adhesive A cannot be applied along the approximately entire circumference. Thus, sufficient bonding strength cannot be obtained. Further, if the maximum height from the outer peripheral surface 3a of the embedded part 3 is less than 0.01 mm, the heights of the projecting line parts 5 are not enough, so that even if the top parts 5a of the projecting line parts 5 are respectively in contact with the bottom part Bb of the concave groove formed in the embedding hole Ba, the embedded part 3 come to be off easily. Thus, it may be difficult to fix the position of the embedded part 3. Furthermore, when the height exceeds 0.2 mm, the height of the projecting line part 5 is higher than necessary. Thus, in order to correspond to the projecting line parts 5, the bottom part Bb of the concave groove need to be cut deeply with respect to the ceramics block B having low strength. Thus, the ceramics block B may be broken easily.

Further, if three projecting line parts 5 are formed on the outer peripheral surface 3a of the embedded part 3, the dental abutment can be processed easily although it is comparatively small, so that it is preferable. Furthermore, in such an embodiment that three projecting line parts 5 are formed, when the projecting line parts 5 are respectively formed at equal intervals so that the angle between the adjacent projecting line parts 5 and 5 comes to be 120° although this embodiment is not illustrated, the dental adhesive A can be uniformly coated between the adjacent projecting line parts 5 and 5. Thus, since the dental abutment can be certainly fixed at the block B, it is preferable. Further, as illustrated in FIGS. 1 to 4, when each projecting line part 5 is formed so that the angle between the adjacent projecting line parts 5 and 5 comes to be 150°, 150° and 60°, the position at which each of the projecting line parts 5 is in contact with the concave groove of the embedding hole Ba is only one. Thus, the attachment position of the dental abutment is not mistaken. Furthermore, if the projecting line parts 5 have such an angle, there are no portions where the interval between the adjacent projecting line parts is too narrow. Thus, the bonding strength is not damaged, so that it is preferable.

For actually producing a dental prosthesis using such a dental abutment according to the present invention, for example, the dental abutment according to the present invention as illustrated in FIGS. 1 to 4 is produced and prepared by cutting a cylindrical material, a rod-like material or the like at first. As the material of the dental abutment, any material is available if it has strength and safety that can be used in an oral cavity. For example, metals such as titanium, titanium alloy, and the like can be used.

Then, three-dimensional shape data of a dental prosthesis is created by, for example, collecting an impression including a portion at which an implant fixture is embedded in an oral cavity of a patient, producing a gypsum model from the impression, measuring the gypsum model with a three-dimensional measuring apparatus, and creating the three-dimensional shape data of a dental prosthesis by using a computer or the like with respect to the three-dimensional shape data of the gypsum model. Or, the three-dimensional shape data of a dental prosthesis is created by building a dental wax on the gypsum model to produce a desired shape of a dental prosthesis, and then measuring the shape by using the three-dimensional measuring apparatus.

Further, data of the fitting part 2, which is fitted at the end part on the intraoral side of the implant fixture so as not to rotate, is used. These data are created and input in advance on the three-dimensional shape data of a dental prosthesis. Further, if the three-dimensional shape data of the dental abutment according to the present invention is also created and input in advance, the position for embedding the embedded part 3 of the dental abutment in the block B can be determined from the position of the fitting part 2 of the dental abutment created on the three-dimensional shape data of the dental prosthesis. From the determined position for embedding the embedded part 3, the three-dimensional shape data of the position of the embedding hole Ba formed at the block B can be obtained. In addition, a coping (a member for a dental prosthesis) or the like is generally produced from the block B made of ceramics such as zirconia or the like. Thus, actually, three-dimensional shape data of the coping, or the like is further created from the three-dimensional shape data of a dental prosthesis.

Further, a rectangular solid-shaped ceramics block B is mounted on a machine, and the block is cut based on, for example, the three-dimensional shape data of the coping and the three-dimensional shape data of the embedding hole Ba, so that the coping portion and the embedding hole Ba can be cut at once. In addition, although it is not illustrated, the block B has a holding part such as a shaft or the like, which restricts the mounting direction to be a correct direction and the block B not to rotate when the block B is mounted on the machine, so that the position at a time of cutting the block B can be aligned easily.

Figure 5:
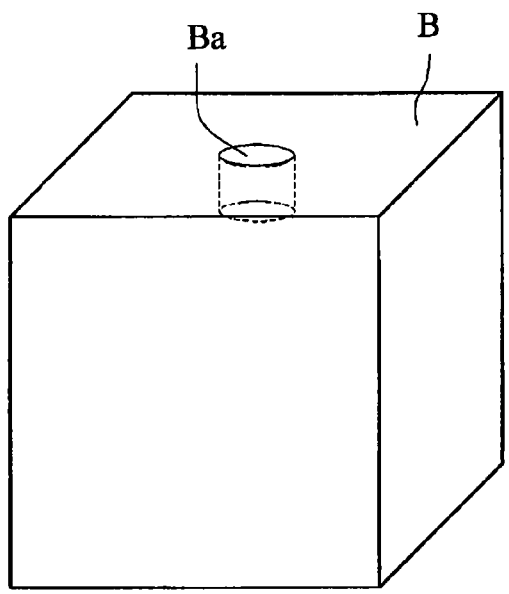
FIG. 5 is a perspective view of a block in which an embedding hole is formed in advance.

As the block B to be used, the block B where the embedding hole Ba is formed in advance as illustrated in FIG. 5 can be used. For example, when the block B itself is made of a metal mold or the like, the embedding hole Ba is a standard shape not depending on each patient, so that the embedding hole Ba can be formed simultaneously by the metal mold or the like. Thus, since it is not necessary to cut the embedding hole Ba having a same shape many times, it is very efficient. In addition, the ceramics block B to be used is a sintered body. Thus, after sintering, some dimension errors may occur at the embedding hole Ba formed in advance. However, the embedding hole Ba is not a portion to fit to the embedded part 3 of the dental abutment but a portion to insert the embedded part 3 and form a gap between the dental abutment and the block B. Thus, if the dimension errors are some, that does not matter as compared with a case in which the embedding hole Ba is a portion to fit to the embedded part 3.

Further, in the case of cutting such block B where the embedding hole Ba is formed in advance, three-dimensional shape data of a coping or the like and three-dimensional shape data of the embedding hole Ba are used, so that the coping or the like can be cut by a cutting machine in a state of correctly reflecting the positional relationship with the embedding hole Ba.

Furthermore, for actually performing a treatment by using the coping or the like produced by the above processing, only the dental abutment according to the present invention is fixed at the implant fixture at first. That is, the fitting part 2 of the dental abutment according to the present invention is fitted to the end part on the intraoral side of the implant fixture embedded in the jawbone so that the dental abutment does not rotate. In addition, the bolt is inserted to penetrate the through hole 4, and is screwed into a female thread screwed in the implant fixture, so that the dental abutment can be fixed at the implant fixture.

Then, the dental adhesive A is coated to the outer peripheral surface 3a of the embedded part 3 of the dental abutment fitted and fixed at the implant fixture, or to the inner surface Bc of the embedding hole Ba of the coping or the like made of the block B in advance, and then the embedded part 3 of the dental abutment is inserted into the embedding hole Ba of the coping or the like, so that the dental abutment is bonded and fixed. At this time, the top parts 5a of the three or more projecting line parts 5 of the dental abutment are respectively in contact with the bottom part Bb of the concave groove formed in the embedding hole Ba of the coping or the like, so that each projecting line part 5 is induced along the concave groove. Thus, the dental abutment can be accurately inserted into a predetermined position.

Furthermore, in another treatment method, a bolt insertion through hole which is continued coaxially is cut on the embedding hole Ba in advance, and the dental prosthesis member or the like and the dental abutment according to the present invention are bonded and fixed in advance by the dental adhesive A. Then, the bolt penetrates the bolt insertion through hole formed at the coping or the like, and is inserted until the head of the bolt is in contact with the step part 4a in the through hole 4, and is screwed and fixed into a female thread screwed in the implant fixture, and the bolt insertion through hole of the coping or the like is filled with a dental cement or the like. Accordingly, attaching the dental abutment to the implant fixture is completed.

What is claimed is:
1. A set comprising:
a dental abutment; and
a ceramics block from which a dental prosthesis is to be cut or the dental prosthesis cut from the ceramics block,
wherein the dental abutment includes:
a gingiva contact part having a truncated conical shape that increases in thickness going from a first end of the gingiva contact part, which is a surface configured to face toward a jawbone and to be in contact with an end surface of an implant fixture, to a second end of the gingiva contact part;
a fitting part configured to project toward the jawbone from the first end of the gingiva contact part, and configured to fit into an end part of the implant fixture so as not to rotate; and
an embedded part projecting toward a direction opposite to a projecting direction of the fitting part from the second end of the gingiva contact part,
wherein a center axis of the gingiva contact part, a center axis of the fitting part, and a center axis of the embedded part are coaxial,
wherein a through hole penetrates the gingiva contact part, the fitting part, and the embedded part, and the through hole is configured so that a bolt is insertable through the through hole to be screwed into a female thread screwed in the implant fixture, wherein a step that is configured to be in contact with a head of the bolt is formed in the through hole, and a center axis of the through hole is coaxial with the center axes of the gingiva contact part, the fitting part, and the embedded part, wherein three or more projecting line parts each having a same shape are formed on an outer peripheral surface of the embedded part, and each of the projecting line parts starts from the second end of the gingiva contact part, and projects in a longitudinal direction that is parallel with the center axis of the embedded part, wherein the ceramics block from which the dental prosthesis is to be cut or the dental prosthesis cut from the ceramics block includes:

an embedding hole formed in advance in the ceramics block from which the dental prosthesis is to be cut or formed when the ceramics block is cut to be the dental prosthesis, and when the embedded part is embedded into the embedding hole of the ceramics block from which the dental prosthesis is to be cut or formed when the ceramics block is cut to be the dental prosthesis, a uniform gap for a dental adhesive including a width of 5 to 100 μm is formed along an approximately entire circumference between an inner surface of the embedding hole and an outer peripheral surface of the embedded part in a condition that top parts of the projecting line parts are in contact with respective bottom parts of concave grooves formed in the embedding hole.

2. The set according to claim 1,
wherein one of the projecting line parts has a length of 0.05 to 3 mm, a width of 0.05 to 0.2 mm and a maximum height from the outer peripheral surface of the embedded part of 0.01 to 0.2 mm.

3. The set according to claim 2,
wherein three projecting line parts are formed on the outer peripheral surface of the embedded part.

4. The set according to claim 3,
wherein the projecting line parts are respectively formed at equal intervals so that an angle between adjacent projecting line parts is 120°.

5. The set according to claim 3,
wherein the projecting line parts are respectively formed so that angles between adjacent projecting line parts are 150°, 150° and 60°.

6. The set according to claim 1,
wherein three projecting line parts are formed on the outer peripheral surface of the embedded part.

7. The set according to claim 6,
wherein the projecting line parts are respectively formed at equal intervals so that an angle between adjacent projecting line parts is 120°.

8. The set according to claim 6,
wherein the projecting line parts are respectively formed so that angles between adjacent projecting line parts are 150°, 150° and 60°.

* * * * *